(12) United States Patent
Kuechler et al.

(10) Patent No.: US 9,464,020 B2
(45) Date of Patent: Oct. 11, 2016

(54) PROCESS FOR PRODUCING PHENOL AND CYCLOHEXANONE

(71) Applicant: ExxonMobil Chemical Patents Inc., Baytown, TX (US)

(72) Inventors: Keith H. Kuechler, Friendswood, TX (US); Francisco M. Benitez, Cypress, TX (US); Krystle J. Emanuele, Houston, TX (US); Christopher L. Becker, Manhattan, KS (US); John L. Heidman, Jr., Manassas, VA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/394,208

(22) PCT Filed: Apr. 9, 2013

(86) PCT No.: PCT/US2013/035799
§ 371 (c)(1),
(2) Date: Oct. 13, 2014

(87) PCT Pub. No.: WO2013/165659
PCT Pub. Date: Nov. 7, 2013

(65) Prior Publication Data
US 2015/0065753 A1 Mar. 5, 2015

Related U.S. Application Data

(60) Provisional application No. 61/641,374, filed on May 2, 2012.

(30) Foreign Application Priority Data

Jun. 14, 2012 (EP) .................................... 12172046

(51) Int. Cl.
C07C 45/53 (2006.01)
C07C 37/08 (2006.01)
(Continued)

(52) U.S. Cl.
CPC ............... *C07C 45/83* (2013.01); *B01D 3/40* (2013.01); *B01D 11/00* (2013.01); *C07C 2/74* (2013.01); *C07C 37/08* (2013.01); *C07C 37/80* (2013.01); *C07C 41/01* (2013.01); *C07C 41/56* (2013.01);
(Continued)

(58) Field of Classification Search
CPC .......... C07C 45/53; C07C 37/08; C07C 2/66
USPC ......... 568/342, 347, 591, 606, 798; 585/467
See application file for complete search history.

(56) References Cited

U.S. PATENT DOCUMENTS

| 2,265,939 A | 12/1941 | Field |
| 4,230,638 A | 10/1980 | Murtha |

(Continued)

FOREIGN PATENT DOCUMENTS

| EP | 0 293 032 | 11/1988 |
| WO | WO 97/17290 | 5/1997 |

(Continued)

OTHER PUBLICATIONS

Charette et al., Chapter 1, "*Simmons-Smith Cyclopropanation Reaction*," Organic Reactions (Hoboken, NJ, United States), 58, pp. 1-419, Oct. 23, 2012.

(Continued)

*Primary Examiner* — Sikarl Witherspoon
(74) *Attorney, Agent, or Firm* — Siwen Chen; Stephen A. Baehl

(57) ABSTRACT

In a process for separating a mixture comprising cyclohexanone and phenol, at least a portion of the mixture is distilled in the presence of a solvent including at least two alcoholic hydroxyl groups attached to non-adjacent saturated carbon atoms and at least one hemiketal defined by the formula (I) or the formula (II):

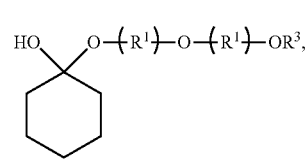

(I)

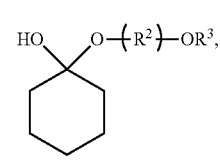

(II)

wherein $R^1$, the same or different at each occurrence, is independently an alkylene group having from 2 to 10 carbon atoms, $R^2$ is an alkylene group having from 4 to 10 carbon atoms, and $R^3$ is hydrogen or the following group:

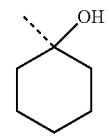

and/or an enol-ether derived from the hemiketal defined by the formula (I) or the formula (II), wherein the total concentration of the hemiketal and the enol-ether, expressed in terms of weight percentage on the basis of the total weight of the feed to the distilling step (a), is at least 0.01%.

20 Claims, 6 Drawing Sheets

(51) Int. Cl.
    *C07C 45/83*     (2006.01)
    *C07C 37/80*     (2006.01)
    *C07C 41/01*     (2006.01)
    *C07C 41/56*     (2006.01)
    *C07C 43/188*     (2006.01)
    *C07C 43/196*     (2006.01)
    *C07C 43/317*     (2006.01)
    *B01D 3/40*     (2006.01)
    *B01D 11/00*     (2006.01)
    *C07C 2/74*     (2006.01)
    *C07C 407/00*     (2006.01)
    *C09K 3/00*     (2006.01)

(52) U.S. Cl.
    CPC ........... *C07C 43/188* (2013.01); *C07C 43/196* (2013.01); *C07C 43/317* (2013.01); *C07C 45/53* (2013.01); *C07C 407/00* (2013.01); *C09K 3/00* (2013.01); *C07C 2101/14* (2013.01)

(56) References Cited

U.S. PATENT DOCUMENTS

| | | |
|---|---|---|
| 4,351,967 A | 9/1982 | Nishimura et al. |
| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,334,774 A | 8/1994 | Kogure et al. |
| 5,362,697 A | 11/1994 | Fung et al. |
| 6,037,513 A | 3/2000 | Chang et al. |
| 6,049,018 A | 4/2000 | Calabro et al. |
| 6,077,498 A | 6/2000 | Diaz Cabanas et al. |
| 6,720,462 B2 | 4/2004 | Kuhnle et al. |
| 6,756,030 B1 | 6/2004 | Rohde et al. |

FOREIGN PATENT DOCUMENTS

| | | |
|---|---|---|
| WO | WO 2009/025939 | 2/2009 |
| WO | WO 2009/058527 | 5/2009 |
| WO | WO 2009/058531 | 5/2009 |
| WO | WO 2009/131769 | 10/2009 |
| WO | WO 2013/052216 | 4/2013 |

OTHER PUBLICATIONS

Deslongchamps et al., "5. Formation of Cyclic Ketals from Hydroxyalkyl Enol Ethers, a Stereoelectronically Controlled endo-trig-Cyclization Process," Helvetica Chimica Acta, vol. 79, No. 1, 7 Feb. 1996, pp. 41-50.

Sugimura et al., "Chiral and Flexible 2,4-pentanediol-tethered Cyclopropanation of Olefins with a Carbenoid Derived from a Diazo Ester to Construct Three Stereogenic Center," Tetrahedron: Asymmetry, Pergamon Press Ltd, Oxford, GB, vol. 14, No. 7, Apr. 4, 2003, pp. 881-890.

Sugimura et al., "Temperature-independent Stereoselectivity in Intramolecular Cycloaddition of Ketene Generated from Diazoester in Solution and in Vapor Phase: How Entrophy Terms Governs the Selectivity," Bulletion of the Chemical Society of Japan, vol. 85, No. 4, Mar. 28, 2012, pp. 504-510. (English Abstract only).

Sugimura et al., "Total Syntheses of (+)-Ipomeamarone and (−)-Ngaione via Novel Intramolecular Hydrogen Abstraction," Tetrahedron, vol. 50, No. 40, Jan. 1, 1994, pp. 11647-11658.

US 9,464,020 B2

PROCESS FOR PRODUCING PHENOL AND CYCLOHEXANONE

PRIORITY CLAIM TO RELATED APPLICATIONS

This application is a National Stage Application of International Application No. PCT/US2013035799 filed Apr. 9, 2013, which claims priority to and the benefit of U.S. Provisional Application Ser. No. 61/641,374 filed May 2, 2012 and European Application No. 12172046.0 filed Jun. 14, 2012, the disclosures of which are fully incorporated herein by their reference.

FIELD

The present invention relates to a process for producing phenol and cyclohexanone. In particular, the present invention relates to an extractive distillation process for separating a mixture of phenol and cyclohexanone. The present invention is useful, e.g., in producing cyclohexanone and phenol from benzene alkylation in the presence of hydrogen.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide in the presence of heterogeneous or homogeneous catalysts into equimolar amounts of phenol and acetone, a co-product. However, the world demand for phenol is growing more rapidly than that for the acetone co-product. In addition, due to developing shortages in supply, the cost of propylene is likely to increase.

Thus, a process that avoids, or reduces the use of propylene as a feed and coproduces higher ketones, rather than acetone, may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone co-product in roughly equimolar amounts.

There are, however, a number of problems associated with producing phenol via cyclohexylbenzene rather than the cumene-based Hock process. One such problem is that the cyclohexanone and phenol produce an azeotropic mixture composed of 28 wt % cyclohexanone and 72 wt % phenol. Thus, while some high purity cyclohexanone can be recovered from the product of the '513 patent by simple distillation, production of high purity phenol requires a different separation approach.

One convenient approach is by extractive distillation. This method uses a solvent, which desirably has a lower volatility than the lowest volatility of the component in the mixture to be separated, is miscible with the mixture and the components therein, and does not form an azeotrope with the mixture or any of its components. Conveniently, the solvent interacts differently with the components of the azeotropic mixture thereby causing their relative volatilities to change. This enables the new three-part system to be separated in a simple distillation device or devices. The original component with the greatest volatility separates out as the top product, while the bottom product comprises the solvent and the lower volatility component. This bottoms product can again be separated easily because the solvent doesn't form an azeotrope with the lower volatility component.

Various solvents have been proposed for the separation of azeotropic phenol systems over the years. For example, for the phenol-cyclohexanone system, U.S. Pat. No. 2,265,939 discusses the use of diols and glycols as a solvent. This patent notes that ethylene glycol will react with the cyclohexanone to form ketals which co-distill with cyclohexanone, and recovery of the reacted cyclohexanone and ethylene glycol must be effected by conducting a hydrolysis reaction. It further notes that to avoid the reaction of cyclohexanone and the solvent, larger molecules providing a greater atomic distance between the two hydroxyl groups of a diol or glycol, such as diethylene glycol, should be employed.

U.S. Pat. No. 5,334,774 discusses the use of diethylene glycol to effect separation between the azeotropic system of phenol and sec-butylbenzene.

In U.S. Pat. No. 4,230,638, mixtures of sulfolane, diethylene glycol, and non-oxygenated hydrocarbons are proposed as solvents in a liquid-liquid extraction system for the separation of cyclohexylbenzene from phenol and cyclohexanone. However, sulfolane, while having outstanding solvent qualities for this separation, is not preferred due to its high reactivity with oxygen. Air ingress is difficult to avoid in any distillation process conducted at vacuum pressures and, with sulfolane as a solvent, can result in the production of acids and other deleterious degradation products. Diols and glycols tend to be preferred as they are far more resistant to undesirable side-reactions with oxygen.

According to the present disclosure, it has now been found that diols and glycols having their hydroxyl groups attached to non-adjacent carbon atoms can undergo a reaction with cyclohexanone to form a previously undocumented class of hemiketal and enol-ether condensation products under certain conditions. Specifically, we have uncovered the formation of large acyclic hemiketals, and also their cyclic olefin/ether water elimination products (enol-ethers) under certain conditions, which can affect the separation of phenol and cyclohexanone. Recognition of this fact, and the characteristics of these new compounds, is important to the proper design and operation of extractive distillation systems for the separation of phenol and cyclohexanone using such larger diols and glycols as solvents in general, and diethylene glycol in particular.

SUMMARY OF THE INVENTION

In a first aspect, the present disclosure relates to a composition of matter comprising a hemiketal defined by the formula (I) or the formula (II):

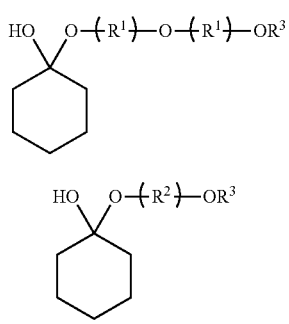

(I)

(II)

wherein $R^1$, the same or different at each occurrence, is independently an alkylene group having from 2 to 10 carbon atoms, $R^2$ is an alkylene group having from 4 to 10 carbon atoms, and $R^3$ is hydrogen or the following group:

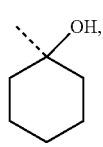

and/or an enol-ether derived from the hemiketal defined by the formula (I) or the formula (II), wherein the total concentration of the hemiketal and enol-ether, expressed in terms of weight percentage on the basis of the total weight of the feed to the distilling step (a), is at least 0.01%.

In certain embodiments, $R^1$ is an alkylene group having 2 carbon atoms (an ethylene group) and $R^2$ is an alkylene group having 4 carbon atoms (an 1,4-butanediyl group).

In a second aspect, the present disclosure relates to a composition of matter comprising a hemiketal defined by the formula (III):

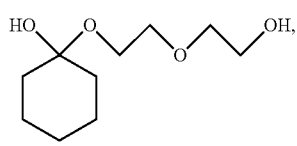

(III)

and/or an enol-ether thereof defined by the formula (IV):

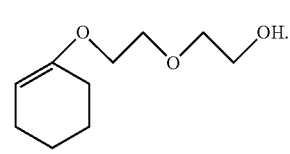

(IV)

In a third aspect, the present disclosure relates to a composition of matter comprising a hemiketal defined by the formula (V):

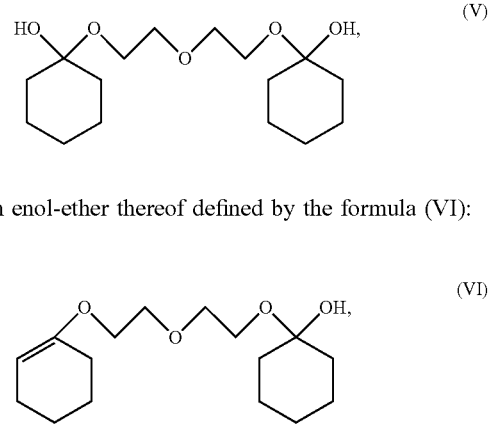

(V)

and/or an enol-ether thereof defined by the formula (VI):

(VI)

and/or an enol-ether thereof defined by the formula (VII):

(VII)

In a fourth aspect, the present disclosure relates to a composition of matter comprising a hemiketal defined by the formula (VIII):

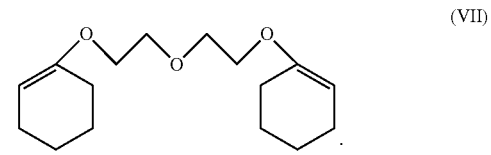 [SMILES: C1=C(OCCOCCOC2=CCCCC2)CCCC1]

(VIII)

and/or an enol-ether thereof defined by the formula (IX):

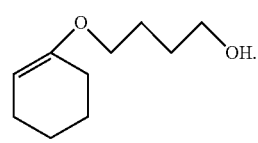

(IX)

In a fifth aspect, the present disclosure relates to a composition of matter comprising a hemiketal defined by the formula (X):

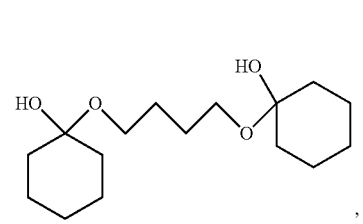

(X)

and/or an enol-ether thereof defined by the formula (XI):

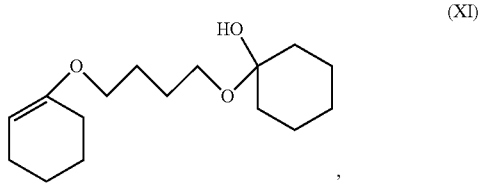 [SMILES: OC1(OCCCCOC2=CCCCC2)CCCCC1]
(XI)

and/or an enol-ether thereof defined by the formula (XII):

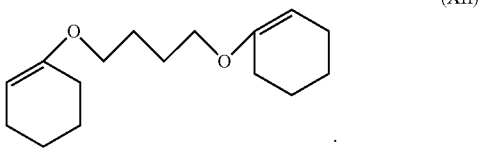
(XII)

In a sixth aspect, the present disclosure relates to a process for separating a mixture comprising cyclohexanone and phenol which comprises (a) distilling at least a portion of the mixture in the presence of a solvent including at least two alcoholic hydroxyl groups attached to non-adjacent saturated carbon atoms and at least one hemiketal defined by one the formulae (I), (II), (III), (V), (VIII), and (X) or an enol-ether defined by one the formulae (IV), (VI), (VII), (IX), (XI), and (XII).

In seventh aspect, the present disclosure is related to a process for making cyclohexanone and phenol, the process comprising:

(A) contacting benzene and hydrogen with a catalyst under hydroalkylation conditions to produce a first effluent comprising cyclohexylbenzene;

(B) oxidizing at least part of the cyclohexylbenzene in the first effluent to produce a second effluent comprising cyclohexylbenzene hydroperoxide;

(C) cleaving at least part of the cyclohexylbenzene hydroperoxide in the second effluent stream to obtain a product mixture comprising phenol and cyclohexanone; and (D) separating the product mixture by (a) distilling at least a portion of the mixture in the presence of a solvent including at least two alcoholic hydroxyl groups attached to non-adjacent saturated carbon atoms and at least one hemiketal defined by one of the formulae (I), (II), (III), (V), (VIII), and (X) or an enol-ether defined by one of the formulae (IV), (VI), (VII), (IX), (XI), and (XII).

In certain embodiments, at least a portion of said hemiketal and/or enol-ether is formed from the reaction of cyclohexanone and said solvent during said distilling.

In certain advantageous embodiments, said distilling step (a) is conducted in the presence of water.

In one embodiment, said distilling step (a) separates the mixture into a first stream rich in cyclohexanone and a second stream rich in phenol; the solvent and said hemiketal and/or enol-ether and the process further comprises (b) distilling the second stream to separate at least part of the phenol therefrom and produce a recovered solvent. In certain embodiments, the recovered solvent is recycled to the distilling step (a) and desirably provides at least a portion of the hemiketal and/or enol-ether present in the distilling step (a).

DETAILED DESCRIPTION OF THE EMBODIMENTS

Figure 1:
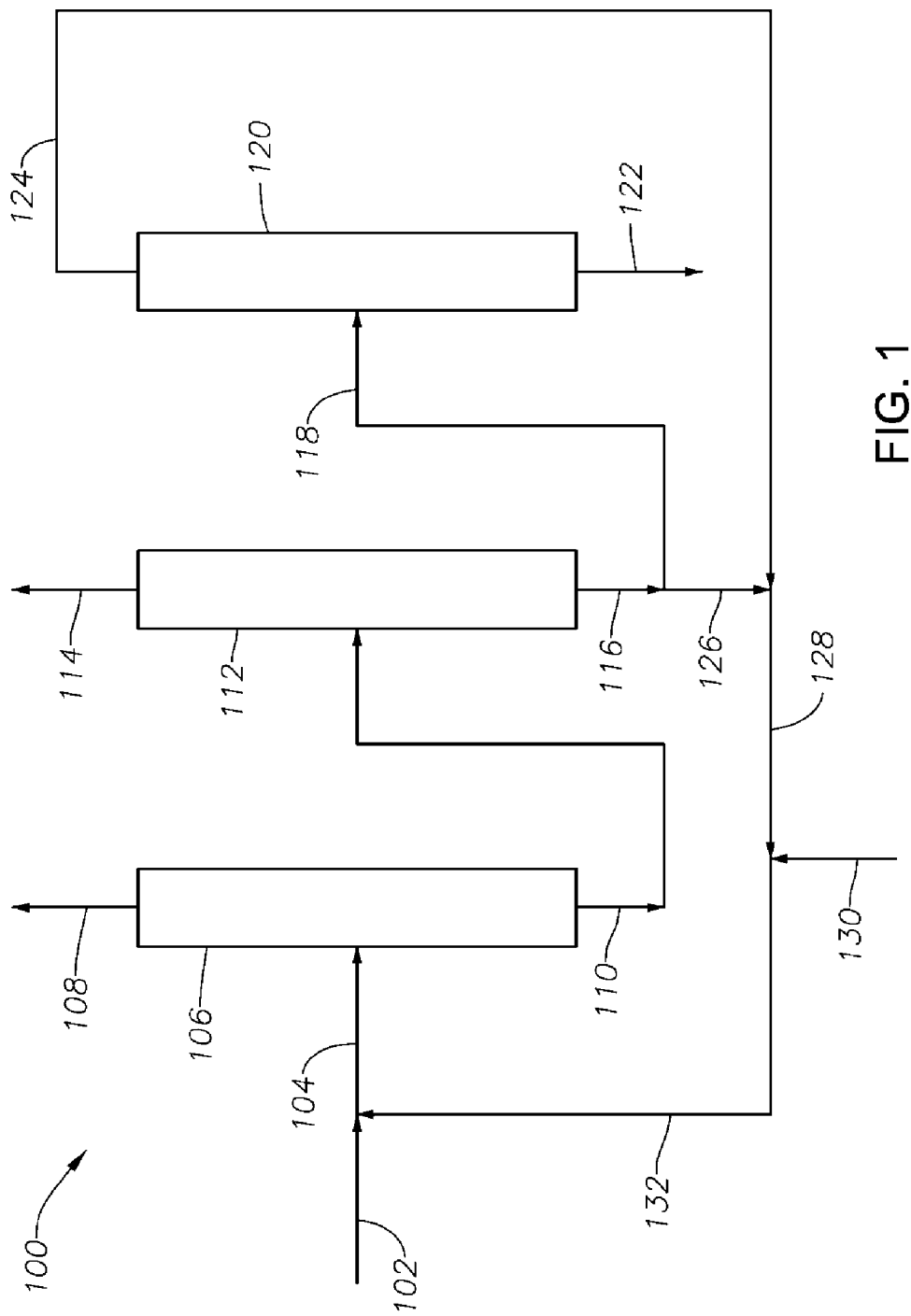
FIG. 1 is a schematic diagram of a process for separating a mixture comprising cyclohexanone and phenol according to a first embodiment of the present disclosure.

Described herein are compositions of matter comprising certain novel hemiketals and enol-ethers formed by the reaction of cyclohexanone and glycol solvents, such as diethylene glycol, during the separation of phenol and cyclohexanone by extractive distillation, under certain distillation conditions, and distillation processes involving such hemiketals and/or enol-ethers. As used herein, the term "hemiketal(s)/enol-ether(s)" means hemiketal(s) or enol-ether(s) individually or combined. Thus, in a composition of matter according to certain embodiments of the present disclosure, there may exist one or more hemiketal, as well as one or more of the corresponding enol-ether of each of the hemiketal.

A process in the present disclosure is described to have multiple "steps," which should be interpreted to mean actions or operations that may occur in the process once or multiple times, continuously or discontinuously. Unless specified to the contrary, or the context clearly indicates otherwise, the various steps/actions/operations may be conducted sequentially as they are listed, in an overlapping fashion, or in any other order, as the case may be.

In one advantageous embodiment, the extractive distillation described herein forms part of an integrated process for producing phenol and/or cyclohexanone from benzene in which the benzene is first converted to cyclohexylbenzene, the cyclohexylbenzene is then oxidized to produce cyclohexylbenzene hydroperoxide, the hydroperoxide is subsequently cleaved to produce phenol and cyclohexanone, and a resultant mixture of phenol and cyclohexanone is separated using the process according to the present disclosure. The ensuing description will therefore focus on this integrated process.

Production of the Cyclohexylbenzene

In the initial step of the integrated process starting from benzene, cyclohexylbenzene is produced by reacting the benzene with cyclohexene in the presence of a catalyst having an alkylation function and under conditions to promote the following reaction:

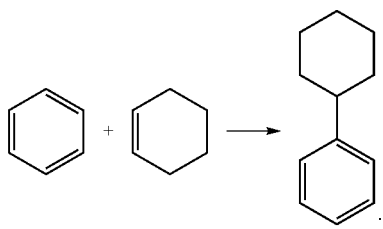

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

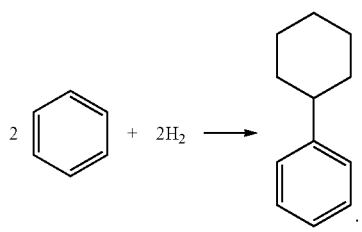 [SMILES: c1ccccc1 ; c1ccc(C2CCCCC2)cc1]

Any commercially available benzene feed can be used in the hydroalkylation step, but in certain advantageous embodiments the benzene has a purity level of at least 99 wt %. Similarly, although the source of hydrogen is not critical, it is desirable that the hydrogen is at least 99 wt % pure.

In certain embodiments, the total feed to the hydroalkylation step contains less than 1000 ppm, such as less than 500 ppm, for example less than 100 ppm, water. In addition, the total feed desirably contains less than 100 ppm, such as less than 30 ppm, for example, less than 3 ppm, sulfur, and less than 10 ppm, such as less than 1 ppm, for example less than 0.1 ppm, nitrogen.

Hydrogen can be supplied to the hydroalkylation step over a wide range of values, but desirably is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Desirably the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it an unwanted by-product of the hydroalkylation reaction.

Although the amount of diluent is not narrowly defined, in certain embodiments the diluent is added in an amount such that the weight ratio of the diluent to the aromatic compound is at least 1:100; for example at least 1:10, but no more than 10:1, desirably no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference.);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56, and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. In certain embodiments, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example, from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and in certain embodiments substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Desirably, the catalyst composite is produced by co-pelletization, in which a mixture of the molecular sieve and the metal-containing inorganic oxide are formed into pellets at high pressure (in certain embodiments, about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays, which can be used as a binder, include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio about of 1:1 to about 5:1.

Dealkylation or cracking is also desirably effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. In certain embodiments, the acid catalyst includes at least one aluminosilicate, aluminophosphate, or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, in certain embodiments, hydrogen is introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst, in certain embodiments, comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium, and compounds and mixtures thereof. Desirably, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Desirably, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 hr$^{-1}$ to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{1-2}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is, in certain embodiments, an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

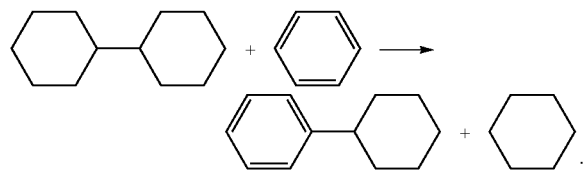

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to remove particulates, air that has been compressed and cooled to condense and remove water, or air that has been enriched in oxygen above the natural approximately 21 mol % in air through membrane enrichment of air, cryogenic separation of air, or other conventional means.

The oxidation is conducted in the presence of a catalyst. Suitable oxidation catalysts include N-hydroxy substituted cyclic imides described in U.S. Pat. No. 6,720,462, which is incorporated herein by reference in its entirety for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxyl substituted cyclic imide or the N,N',N"-trihydroxyisocyanuric acid is employed in an amount between 0.0001 wt % to 15 wt %, such as between 0.001 wt % to 5 wt %, of the cyclohexylbenzene. The use of such oxidation catalysts in the manner disclosed herein conveniently facilitates a high selectivity to the desired cyclohexyl-1-phenyl-1-hydroperoxide, although other hydroperoxides may also be formed in varying quantities and be present in the oxidation effluent.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation effluent. In certain embodiments, the oxidation effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation effluent. The oxidation effluent may further comprise imide catalyst and unreacted cyclohexylbenzene. For example, the oxidation effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation effluent.

At least a portion of the oxidation effluent may be subjected to a cleavage reaction, with or without undergoing any prior separation or treatment. For example, all or a fraction of the oxidation effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide.

In certain embodiments, the acid catalyst used in the cleavage reaction is at least partially soluble in the cleavage effluent, is stable at a temperature of at least 185° C., and has a lower volatility (higher normal boiling point) than cyclohexylbenzene. Desirably, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage effluent contains at least 50 parts-per-million-by-weight (wppm) and no greater than 5000 wppm of the acid catalyst, or at least 100 wppm to and no greater than 3000 wppm, or at least 150 wppm to and no greater than 2000 wppm of the acid catalyst, or at least 300 wppm and no greater than 1500 wppm of the acid catalyst, based upon total weight of the cleavage effluent.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12 and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage effluent may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone. The preferred polar solvent is phenol and/or cyclohexanone recycled from the cleavage product after cooling. In certain embodiments, the polar solvent is added to the cleavage effluent such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage effluent includes cyclohexylbenzene in an amount of at least 50 wt %, or at least 60 wt %, or at least 65 wt %, or at least 70 wt %, or at least 80 wt %, or at least 90 wt %, based upon total weight of the cleavage effluent.

In certain embodiments, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage effluent is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

Separation of Phenol from Cleavage Effluent

The major products of the cleavage reaction of cyclohexyl-1-phenyl-1-hydroperoxide are phenol and cyclohexanone in proportions such that the weight ratio of phenol to cyclohexanone in the cleavage effluent is less than or equal to 2.57, such as, from about 0.7 to about 1.5, for example, from about 0.8 to about 1.2. In other words, the cleavage effluent contains more cyclohexanone than the 28 wt % present in the azeotropic mixture of phenol and cyclohexanone. Thus, simple distillation can be used to remove cyclohexanone from the cleavage effluent and leave an effluent fraction with reduced cyclohexanone content desirably approaching the azeotropic amount of 28 wt %. However, pure phenol cannot be recovered from the cleavage effluent by simple distillation.

To obviate this problem the present process employs extractive distillation in which at least part of the cleavage effluent is combined with a solvent capable of breaking the azeotrope between the phenol and cyclohexanone. The solvent employed includes at least two alcoholic hydroxyl groups attached to non-adjacent saturated carbon atoms, the lowest molecular weight example of which is 1,3-butanediol. In certain advantageous embodiments, larger molecules providing a greater atomic distance between the two hydroxyl groups are employed, and the solvent includes at least two alcoholic hydroxyl groups attached to non-adjacent saturated carbon atoms, wherein the hydroxyl groups are separated by at least 4 atoms, or even at least 5 atoms. Suitable solvents wherein the hydroxyl groups are separated by at least 4 atoms include 1,4-butanediol and 1,4-pentanediol. Suitable solvents wherein the hydroxyl groups are separated by at least 5 atoms include 1,5-pentanediol, diethylene glycol, triethylene glycol or tetraethylene glycol, 2-(2-hydroxy-propoxy)-propan-1-ol, 2-(2-hydroxy-1-methyl-ethoxy)-propan-1-ol, and 4-oxa-2,6-heptandiol. In certain embodiments, the proportion of the solvent relative to the mixture of cyclohexanone and phenol fed to distillation is in the range of 1:10 to 10:1, or 1:5 to 5:1, or 1:1 to 4:1, these proportions being on a weight basis.

The mixture comprising phenol and cyclohexanone to be separated using the process of the present disclosure may contain at least 20 wt %, e.g., at least 30 wt %, at least 40 wt %, at least 50 wt %, at least 60 wt %, at least 70 wt %, at least 80 wt %, at least 90 wt %, even at least 95 wt %, in various embodiments, of phenol and cyclohexanone in total, based on the total weight of the feed.

In addition to the solvent and the cleavage effluent, the mixture employed in the extractive distillation process includes one or more hemiketals defined by the formula (I) or the formula (II):

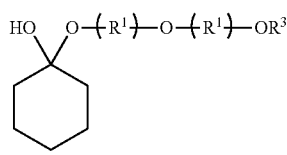
(I)

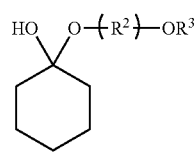
(II)

wherein $R^1$, the same or different at each occurrence, is independently a branched or straight-chain alkylene group having from 2 to 10, in certain embodiments 2, carbon atoms, $R^2$ is a branched or straight-chain alkylene group having from 4 to 10, in certain embodiments 4, carbon atoms, and $R^3$ is hydrogen or the following group:

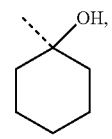

or one or more enol-ethers derived from the hemiketals defined by the formula (I) and the formula (II).

In one embodiment, the hemiketal employed in the extractive distillation process is defined by the formula (III):

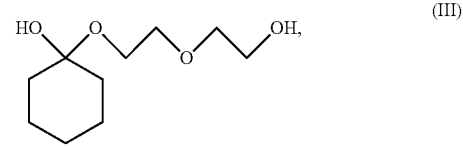 [SMILES: OCCOCCOC1(O)CCCCC1]
(III)

and the enol-ether thereof is defined by the formula (IV):

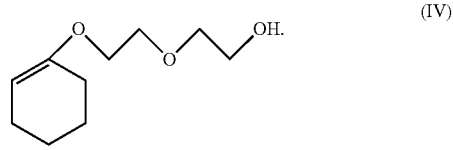 [SMILES: OCCOCCOC1=CCCCC1]
(IV)

In another embodiment, the hemiketal employed in the extractive distillation process is defined by the formula (V):

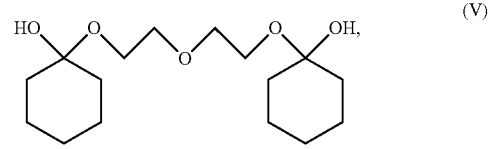 [SMILES: OC1(OCCOCCOC2(O)CCCCC2)CCCCC1]
(V)

and the enol-ether thereof is defined by the formula (VI):

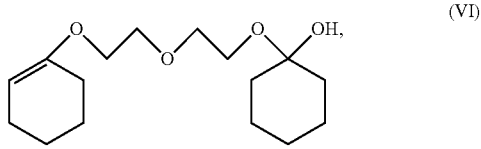 [SMILES: OC1(OCCOCCOC2=CCCCC2)CCCCC1]
(VI)

and/or by the formula (VII):

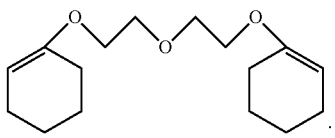
(VII)

In a further embodiment, the hemiketal employed in the extractive distillation process is defined by the formula (VIII):

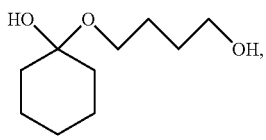
(VIII)

and the enol-ether thereof is defined by the formula (IX):

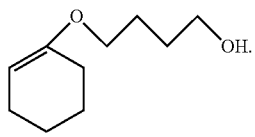
(IX)

In yet a further embodiment, the hemiketal employed in the extractive distillation process is defined by the formula (X):

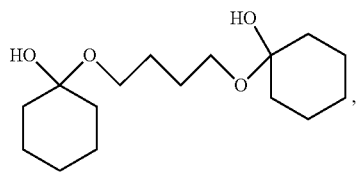
(X)

and the enol-ether thereof is defined by the formula (XI):

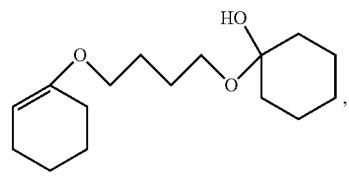
(XI)

and/or by the formula (XII):

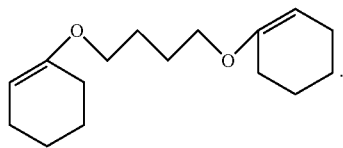
(XII)

It will be appreciated that the hemiketals and enol-ethers described above may be the reaction products of cyclohexanone and the solvent employed in the distillation process, or may be intentionally added into the feed. In particular, the hemiketals and enol-ethers of formulas (III) to (VII) can be the reaction products of cyclohexanone and diethylene glycol, whereas the hemiketals and enol-ethers of formulas (VIII) to (XII) can be the reaction products of cyclohexanone and 1,4-butanediol. The hemiketals and enol-ethers can be partially or completely formed in situ during the distillation process or may be partially or completely produced in a separate reaction between the solvent and cyclohexanone.

Where the hemiketals and enol-ethers described above are produced in a separate reaction between the solvent and cyclohexanone, the reaction is desirably conducted at a temperature in the range of 20° C. to 200° C., such as 70° C. to 180° C., or 90° C. to 160° C. and a pressure in the range of 1 torr to 1000 torr, such as 10 torr to 760 torr, or 40 torr to 400 torr, all absolute (i.e., including vacuum conditions). Note 1 torr=1 mm Hg @ 0° C. The reaction may take place in the presence, or absence, of phenol and/or in the presence, or absence, of a catalyst.

The amount of hemiketal and enol-ether charged or fed to distillation is desirably in the range of at least 0.01 wt % to no greater than 10 wt %, or at least 0.1 wt % to no greater than 5.0 wt %, or at least 1.0 wt % to no greater than 3.0 wt %, with respect to the total weight of cyclohexylbenzene and cyclohexanone, the solvent, and the hemiketal and enol-ether charged or fed to distillation. The amount of the enol-ether present in the whole mixture in the distillation boiler can vary over time during the whole distillation campaign. For example, the total amount of enol-ether in the whole mixture in the distillation boiler can range from 20%-1000%, e.g., 30%-800%, 40%-700%, 50%-500%, 60%-400%, 70%-300%, 80%-200%, of the initial total amount thereof charged into the boiler. Likewise, the total concentration of enol-ether in the whole mixture in the distillation boiler can range from 20%-1000%, e.g., 30%-800%, 40%-700%, 50%-500%, 60%-400%, 70%-300%, 80%-200%, of the initial total concentration thereof charged into the boiler. The variation of the total amount and total concentrations of the enol/ethers in the distillation mixture depends on temperature, pressure, amount of water charged into the mixture, whether the process is batch-based or continuous, and other factors.

The extractive distillation process used to separate the phenol from the cyclohexanone in the cleavage effluent may be conducted in a batch or continuous mode, conveniently continuous.

In a batch distillation process, desirably a charge of material is introduced to a bottoms, reboiler sump of a distillation column, above which there are a number of vapor-liquid contacting trays, culminating in a condenser at the top of the column and means to return some of the liquid overhead product to the top tray as reflux. Heat is applied to the reboiler, generating vapors that rise up the column, and that are condensed by the cooling media in the condenser. The composition of the overhead product withdrawn changes with time, beginning with a composition rich in components of the highest volatility and ending with a composition rich in components of the lowest volatility. Various overhead products cut from the condenser are directed to various dispositions as desired, for example, a set of storage tanks. At a certain point, the distillation is stopped, and a fresh charge of material is again provided to the reboiler sump.

In a continuous distillation process, desirably a continuous feed stream of material is introduced to a distillation column at a tray in between the reboiler at the bottom and the condenser at the top of the column. The bottoms sump and the condenser are fitted with means to continually withdraw a bottoms product and an overhead product, respectively, and again a reflux is provided to the top tray. In continuous distillation, the composition of the bottoms and overhead products generally do not change much with time, so long as the feed stream composition is the same. More than one feed stream may be directed to more than one location in the column, and sidestream products may be withdrawn from trays in between the reboiler and condensor, or the column may be fitted with hip condensors or reboilers to provide cooling or heating to material on trays in between the reboiler and condenser.

The extractive distillation process may be conducted over a wide range of pressure, conveniently in the range of 1 torr to 1000 torr, such as 10 torr to 760 torr, or 30 torr to 300 torr, including 50 torr to 100 torr, all absolute (i.e., including vacuum conditions). Further, conveniently the aforementioned pressures are in the condenser of the distillation column (the very top), and the pressure at the bottoms of the distillation column (desirably the bottoms sump within the column) is higher than that of the condenser by no greater than 100 torr, such as no greater than 60 torr, or even no greater than 30 torr.

Temperatures employed in the extractive distillation may also vary widely, desirably as a function of the selected operating pressure, and the proportions of phenol, cyclohexanone, solvent and enol-ether present in the distillation at any given location or plate, and further as a function of other materials that may be in the distillation, for example cyclohexenone, adipoin (2-hydroxycyclohexanone monomer), bicyclohexyl, or cyclohexylbenzene, potentially entering the distillation with the mixture. Conveniently, the temperatures will be in the range of 60° C. to 190° C., such as 70° C. to 180° C., or 80° C. to 170° C. Further, conveniently the aforementioned temperatures are lowest in the condenser of the distillation column (the very top), and highest at the bottoms of the distillation column (desirably the bottoms sump within the column or exiting a reboiler).

The reflux ratio in the extractive distillation process, that is, the ratio of the rate of reflux flow back to the column from the condensor to the rate of overhead product taken from the condensor, on a weight basis, is desirably in the range of 0.1 to 10, or 0.5 to 5, or 1.0 to 3.0.

Water may be produced during the extractive distillation process by the reaction of cyclohexanone and the solvent to form the enol-ethers described above, but surprisingly, removal of the water during the reaction does not serve to promote additional reaction and generation of the hemiketals and enol-ethers. In fact, addition of water above that naturally produced by the reaction of the cyclohexanone and the solvent can be used to suppress the formation of hemiketals and enol-ethers, and control or prevent the associated loss of the cyclohexonane and solvent. Water may be introduced at any point in the distillation, but conveniently is introduced such that liquid water exists on the trays in the column where there is a substantial presence of both cyclohexanone and the solvent. Conveniently the water is introduced below the lowest feed location, or most conveniently to a location from 1 to 10 trays just above the reboiler, so that the water may be present in most of the column but not present to any great extent, or at all, in the bottoms product.

The water may be introduced in either the liquid or vapor state. In a batch distillation, it is convenient to simply include the desired amount of liquid water in the charge, and it may be convenient to provide means to continuously introduce water into the bottoms sump to ensure it is present in the liquid phase during the time in the distillation when cyclohexanone is still present in the sump, and does not simply all boil off at the beginning of the batch distillation. In a continuous distillation, it is convenient to provide the water as a liquid to the desired feed tray. In these cases, the reboiler provides the heat to vaporize the liquid water and move it up the column to other trays, while the condensor provides the cooling to form liquid water going down the trays, in compositions according to the overall heat and material balance of the column.

The amount of water introduced to the extractive distillation process may vary widely but, in certain embodiments, is at least 0.1 wt % and no greater than 20 wt %, or at least 1 wt % and no greater than 10 wt %, or at least 3 wt % and no greater than 7 wt %, these percentages being with respect to the total weight of feed and all components therein to the distillation column. The reduction in the amount of hemiketals/enol-ethers provided by the introduction of water to the distillation can also vary widely depending on several factors, including the solvent selected, the amount of water added, and the operating conditions and other aspects of the overall heat and material balance of the distillation. For example, the presence of water in the distillation may result in a reduction of at least 1 wt %, or at least 10 wt %, or at least 50 wt %, or at least 80 wt % of that produced by a distillation under the same condition except in the absence of added water. The extent of reduction in enol-ether presence may be gauged by analysis of the bottoms product in a continuous distillation with and without water addition, or of the final reboiler sump product in a batch distillation.

The extractive distillation process separates the feed to the distillation column into at least a first stream, conveniently as an overhead product, that is enriched in the higher volatility components, conveniently including a preponderance of cyclohexanone, and a second stream, conveniently as a bottoms product in a continuous mode, or residue in the sump in a batch mode, that is enriched in the lower volatility components, namely the phenol, solvent, and hemiketals/enol-ethers.

The second stream desirably comprises at least 80 wt %, or at least 90 wt %, or at least 99 wt %, or at least 99.9 wt %, or even all of the phenol in the mixture separated in the distillation process. In addition, the second stream desirably comprises at least 80 wt %, or at least 90 wt %, or at least 99 wt %, or at least 99.9 wt %, of the solvent and no greater than 20 wt %, or no greater than 10 wt %, or no greater than 1 wt %, or no greater than 0.1 wt %, or even no greater than 0.01 wt % of the cyclohexanone in the mixture separated in the distillation process.

In certain embodiments, the second stream may comprise no greater than 1.0 wt %, or no greater than 1000 wppm, or no greater than 100 wppm, or no greater than 10 wppm, or no greater than 1 wppm cyclohexanone. In certain embodiments, it may contain no detectable cyclohexanone. In certain embodiments, the second stream may also comprise from 1 wppm to 10.0 wt % hemiketal or enol-ether individually or combined, or from 10 wppm to 7.0 wt % hemiketal or enol-ether individually or combined, or from 100 wppm to 5.0 wt % hemiketal or enol-ether individually or combined, or from 0.1 wt % to 3.0 wt % hemiketal or enol-ether individually or combined. These quantities are with respect to the total weight of the second stream or aliquot thereof.

The first stream desirably comprises at least 80 wt %, or at least 90 wt %, or at least 99 wt %, or at least 99.9 wt %, or even all of the cyclohexanone in the mixture separated in the distillation process. In addition, the first stream desirably comprises no greater than 20 wt %, or no greater than 10 wt %, or no greater than 1 wt %, or no greater than 0.1 wt % of the phenol and no greater than 20 wt %, or no greater than 10 wt %, or no greater than 1 wt %, or no greater than 0.1 wt % of the solvent separated in the distillation process.

In certain embodiments, the first stream may comprise at least 90.0 wt % or at least 95.0 wt %, or at least 99.0 wt %, or even at least 99.5 wt % cyclohexanone. In certain embodiments, the first stream may also comprise no greater than 1.0 wt %, or no greater than 1000 wppm, or no greater than 100 wppm, or no greater than 10 wppm, or no greater than 1 wppm phenol. Thus, in certain embodiments, it may contain no detectable phenol. The first stream may further comprise no greater than 1.0 wt %, or no greater than 1000 wppm, or no greater than 100 wppm, or no greater than 10 wppm, or no greater than 1 wppm solvent. Hence in certain embodiments, it may contain no detectable solvent. In certain embodiments, the first stream may comprise no greater than 1.0 wt %, or no greater than 1000 wppm, or no greater than 100 wppm, or no greater than 10 wppm, or no greater than 1 wppm hemiketal or enol-ether individually or combined. Hence, in certain embodiments, it may contain no detectable hemiketal or enol-ether. These quantities are with respect to the total weight of the first stream or aliquot thereof.

The first stream formed by the extractive distillation process may provide a cyclohexanone product, or may be subjected to further processing and purification to produce a more refined cyclohexanone product. Such cyclohexanone products may be for use or sales into, say, caprolactam production.

The second stream formed by the extractive distillation process is subjected to further distillation, which can be simple distillation, to divide the second stream into a heavy fraction enriched in lower volatility components, particularly the solvent and hemiketals/enol-ethers, called "recovered solvent," and a light fraction enriched in higher volatility components, particularly the phenol. Desirably, the recovered solvent comprises at least 80 wt %, or at least 90 wt %, or at least 99 wt %, or at least 99.9 wt % of each of the solvent and hemiketals/enol-ethers in the feed to the further distillation process. In addition, the recovered solvent desirably comprises no greater than 20 wt %, or no greater than 10 wt %, or no greater than 1 wt %, or no greater than 0.1 wt % of the phenol in the feed to the further distillation process. In contrast, the light fraction desirably comprises at least 80 wt %, or at least 90 wt %, or at least 99 wt %, or at least 99.9 wt %, or even all of the phenol (and any cyclohexanone) in the feed to the further distillation process. In addition, the light fraction desirably comprises no greater than 20 wt %, or no greater than 10 wt %, or no greater than 1 wt %, or no greater than 0.1 wt %, of the solvent and hemiketals/enol-ethers in the feed to the further distillation process.

In certain embodiments, the recovered solvent may comprise no greater than 1.0 wt %, or no greater than 1000 wppm, or no greater than 100 wppm, or no greater than 10 wppm, or no greater than 1 wppm phenol. It may contain no detectable phenol. Should any cyclohexanone be present in the second stream separated in further distillation, the recovered solvent may comprise no greater than 1.0 wt %, or no greater than 1000 wppm, or no greater than 100 wppm, or no greater than 10 wppm, or no greater than 1 wppm cyclohexanone. Hence, it may contain no detectable cyclohexanone.

The light fraction from the further distillation process may be subjected to further processing and purification to produce a phenol product.

In certain embodiments, the light fraction may comprise no greater than 1.0 wt %, or no greater than 1000 wppm, or no greater than 100 wppm, or no greater than 10 wppm, or no greater than 1 wppm solvent. Hence, in certain embodiments, it may contain no detectable solvent. In certain embodiments, the light fraction may comprise no greater than 1.0 wt %, or no greater than 1000 wppm, or no greater than 100 wppm, or no greater than 10 wppm, or no greater than 1 wppm hemiketal/enol-ether. Hence, in certain embodiments, it may contain no detectable hemiketal/enol-ether. In certain embodiments, should any cyclohexanone be present in the second stream separated in further distillation, the light fraction may comprise no greater than 1.0 wt %, or no greater than 1000 wppm, or no greater than 100 wppm, or no greater than 10 wppm, or no greater than 1 wppm cyclohexanone. Hence, in certain embodiments, it may contain no detectable cyclohexanone.

The recovered solvent may be subjected to a third distillation to separate the solvent from the hemiketals/enol-ethers or part or all of the recovered solvent may be recycled to the extractive distillation column to provide at least some of the solvent and some of the hemiketals/enol-ethers required in the extractive distillation process.

The present disclosure will now be more particularly described with reference to the accompanying drawings. Thus, FIG. 1 is a schematic view of one embodiment of a continuous process 100 for separating phenol and cyclohexanone. In this process, a feedstock mixture comprising phenol and cyclohexanone in line 102 is combined with a solvent/hemiketal/enol-ether stream (including fresh and recovered solvent having at least two alcoholic hydroxyl groups attached to non-adjacent saturated carbon atoms and one or more hemiketals/enol-ethers) in line 132 to form a combined stream in line 104. The combined stream in line 104 is provided to an extractive distillation column 106, which is operated under conditions to separate the combined stream into a first stream as an overhead product in line 108 and a second stream as a bottoms product in line 110.

The first stream in line 108 is richer in cyclohexanone than the combined stream in line 104, for example, containing 99.99 wt % of the cyclohexanone found in the mixture, only 0.01 wt % of the phenol found in the combined stream, and no detectable solvent, hemiketal and enol-ether. The first stream in line 108 may optionally comprise water as may be formed from the reaction of the solvent and cyclohexanone in extractive distillation column 106 to produce hemiketals/enol-ethers or as may be added to extractive distillation column 106 to suppress the reaction of the solvent and cyclohexanone to produce hemiketals/enol-ethers.

The second stream in line 110 is richer in phenol than the combined stream in line 104, for example, containing 99.99 wt % of the phenol found in the mixture, only 0.01 wt % of the cyclohexanone found in the combined stream, the solvent and hemiketals/enol-ether(s). In the extractive distillation column 106, reaction between the solvent, and cyclohexanone may take place depending on, among other things, the proportions of materials present, particularly the quantity of hemiketals/enol-ethers provided to extractive distillation column 106 in line 104, and the operating conditions selected. If the quantity of hemiketal/enol-ether is sufficient, no additional hemiketal/enol-ether may be formed in the distillation column 106, while if the quantity of hemiketal/enol-ether is insufficient, additional hemi-ketal/enol-ether may be formed. Conveniently, there is little or no water in the second stream in line 110.

The second stream in line 110 is provided to a further distillation column, for example, solvent recovery column 112, which is operated under conditions to separate the second stream in line 110 into a light fraction in line 114 and a heavy or "recovered solvent" fraction in line 116. The light fraction is richer in phenol than the second stream in line 110, for example, containing 100% of the cyclohexanone and 99.9 wt % of the phenol found in the second stream, and no detectable solvent, hemiketal, and/or enol-ether. The recovered solvent fraction in line 116 is richer in solvent and hemiketals/enol-ethers than the second stream in line 110, for example, containing substantially all of the solvent and hemiketals/enol-ethers found in the second stream, and only 0.1 wt % of the phenol found in the second stream.

A first portion of the recovered solvent in line 116 is taken in line 118, and provided to third distillation column, for example, solvent tailing column 120. Solvent tailing column 120 is operated under conditions to separate the first portion of recovered solvent in line 118 into a heavy purge stream in line 122 and a tailed solvent stream in line 124. The heavy purge stream in line 122 is richer in hemiketals/enol-ethers than the first portion of recovered solvent in line 118, for example, containing 20 wt % of the hemiketals/enol-ethers and 10 wt % of the solvent found in the first portion of recovered solvent. Tailed solvent stream in line 124 is richer in solvent than the first portion of recovered solvent in line 118, for example, containing 80 wt % of the hemiketals/enol-ethers and 90 wt % of the solvent found in the first portion of recovered solvent.

A second portion of recovered solvent in line 116, for example, comprising the balance of the recovered solvent in line 116, is taken by line 126 and is combined with the tailed solvent in line 124 to form a recycle solvent stream in line 128. The recycle solvent stream in line 128 is further combined with fresh solvent in line 130 to form the solvent/hemiketal stream in line 132 discussed above.

The present disclosure will now be described with reference to the following non-limiting Examples.

The materials used in the Examples were ACS Grade ≥99% cyclohexanone, redistilled ≥99% phenol, ReagentPlus 99% diethylene glycol (DEG), and anhydrous 99.3% ethylene glycol.

Example 1

A glassware set-up consisted of a 250 or 500 mL round-bottom flask attached to a condensing tube to allow the charged liquid to boil and then condense and return to the pot. The system was blanketed in nitrogen and maintained at atmospheric pressure with the use of a glass bubbler filled with mineral oil. The round-bottom flask was immersed in an oil bath to heat it to the appropriate temperature. The oil bath was raised to immerse the flask using a lab jackstand. Temperature in the oil bath was controlled to maintain an appropriate temperature in the round-bottom flask. A stirrer bar was placed in the round-bottom flask to ensure that the system was well-mixed and temperature was consistent. Samples were taken through the sample port, which was a high-temperature silicon septum using an angled needle, valve, syringe assembly. In addition to this set-up a Dean-Stark trap was attached during some experiments to capture any water that was generated or solvent used during the experiments.

100 gram mixtures, of reactants, reactants and solvents, or reactants and catalyst, were charged to the round-bottom flask after being weighed and recorded. The flask was then attached to the glassware assembly as described above. Once attached, nitrogen flow was started to blanket the reaction and heating begun. The mixture was heated and refluxed for an allotted amount of time, desirably ranging between 1.5 and 10 hours. Temperatures ranged from about 130° C. to 200° C., and pressures were atmospheric.

During heating and/or after heating and allowing the solution to cool, samples were taken for analysis by gas chromatography (GC), gas chromatography-mass spectrometry (GC-MS), Karl Fischer (KF), and/or infrared analysis (IR) to observe any signs of the reaction of cyclohexanone with the glycol. Signs of reaction included formation of water, as seen through the KF analysis, disappearance of the C=O stretch using IR, or the appearance of a ketal in the GC or GC-MS analysis.

Figure 2:
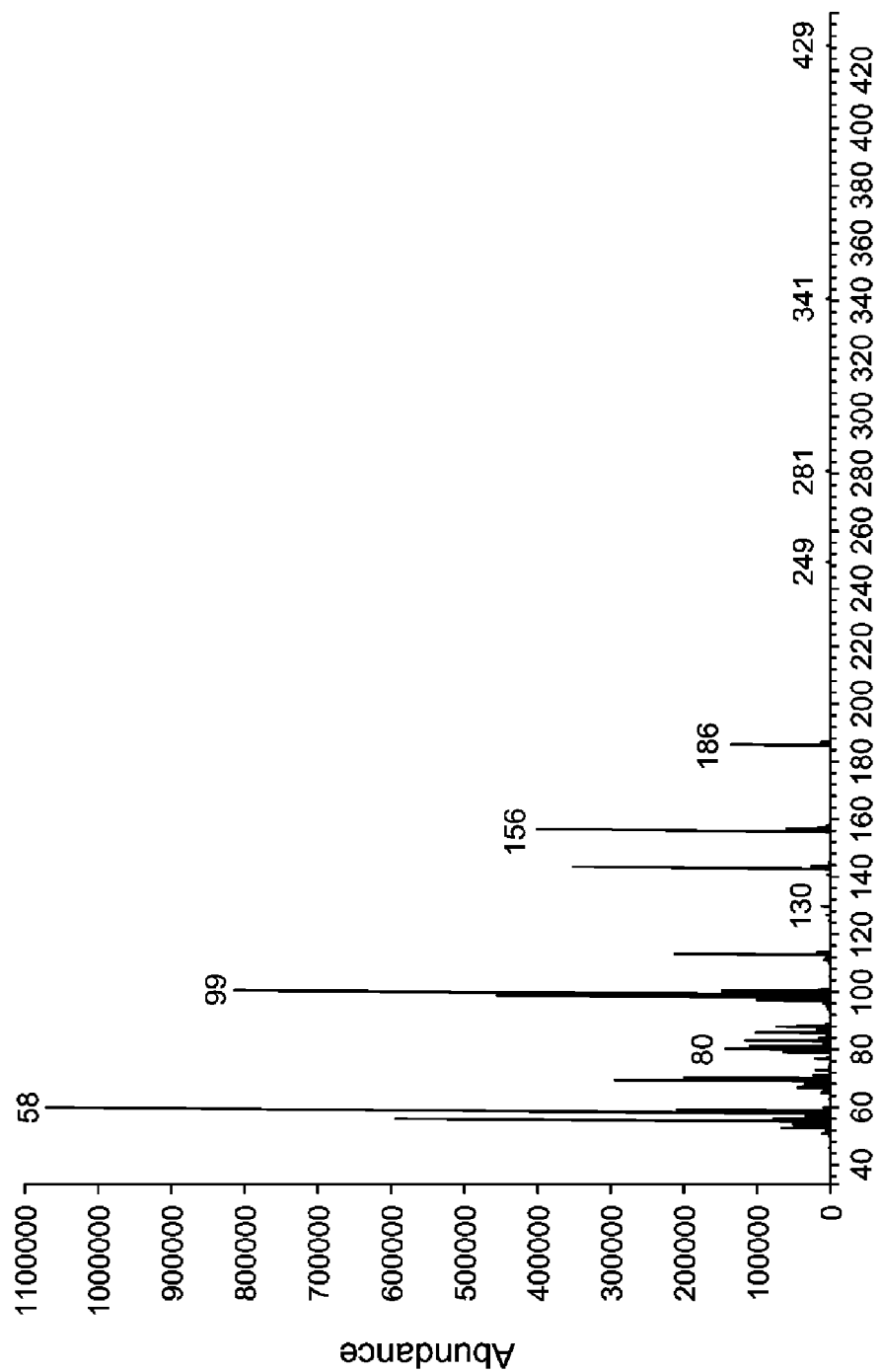
FIG. 2 is the mass spectrograph from GC-MS analysis of the enol-ether of formula (IV) produced according to the process of Example 1.
Figure 3:
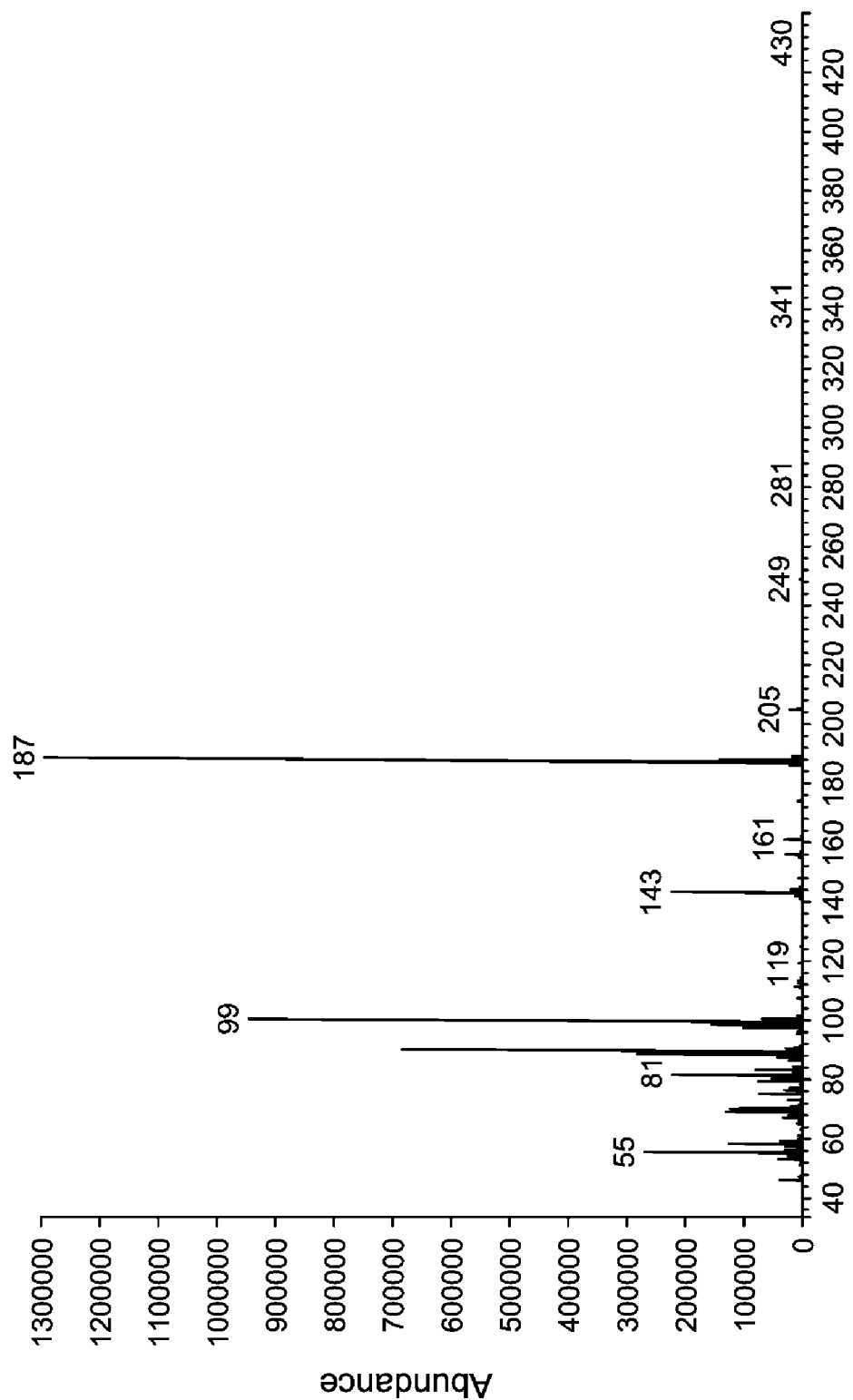
FIG. 3 is the mass spectrograph from GC-MS analysis of the enol-ether of formula (VII) produced according to the process of Example 1.

From an initial charge of 15 wt % cyclohexanone, 15 wt % phenol, and 70 wt % diethylene glycol (DEG), in the absence of any catalyst, refluxed for 8 hours at 153° C., GC-MS analysis of a sample of the reaction product gave peaks at 36.228 and 59.798 minutes with the MS spectrum shown in FIGS. 2 and 3, identified as the enol-ethers of Formulas (IV) and (VII), respectively.

Measurements on the reaction product showed approximately 0.5 wt % of each of the enol-ethers of Formulas (IV) and (VII), and 1000 wppm of water were formed over the 8 hour period.

The above experiment was reproduced in the presence of acid catalysts, including Amberlyst™ 36 Wet solid ion exchange resin, 97% p-toluene sulfonic acid monohydrate, and 98% bismuth (III) subnitrate. Identical species were formed according the GC-MS analyses and other measurements of those experiments, and the quantities of each formed were little different from those formed in the absence of any catalyst.

Example 2

Figure 4:
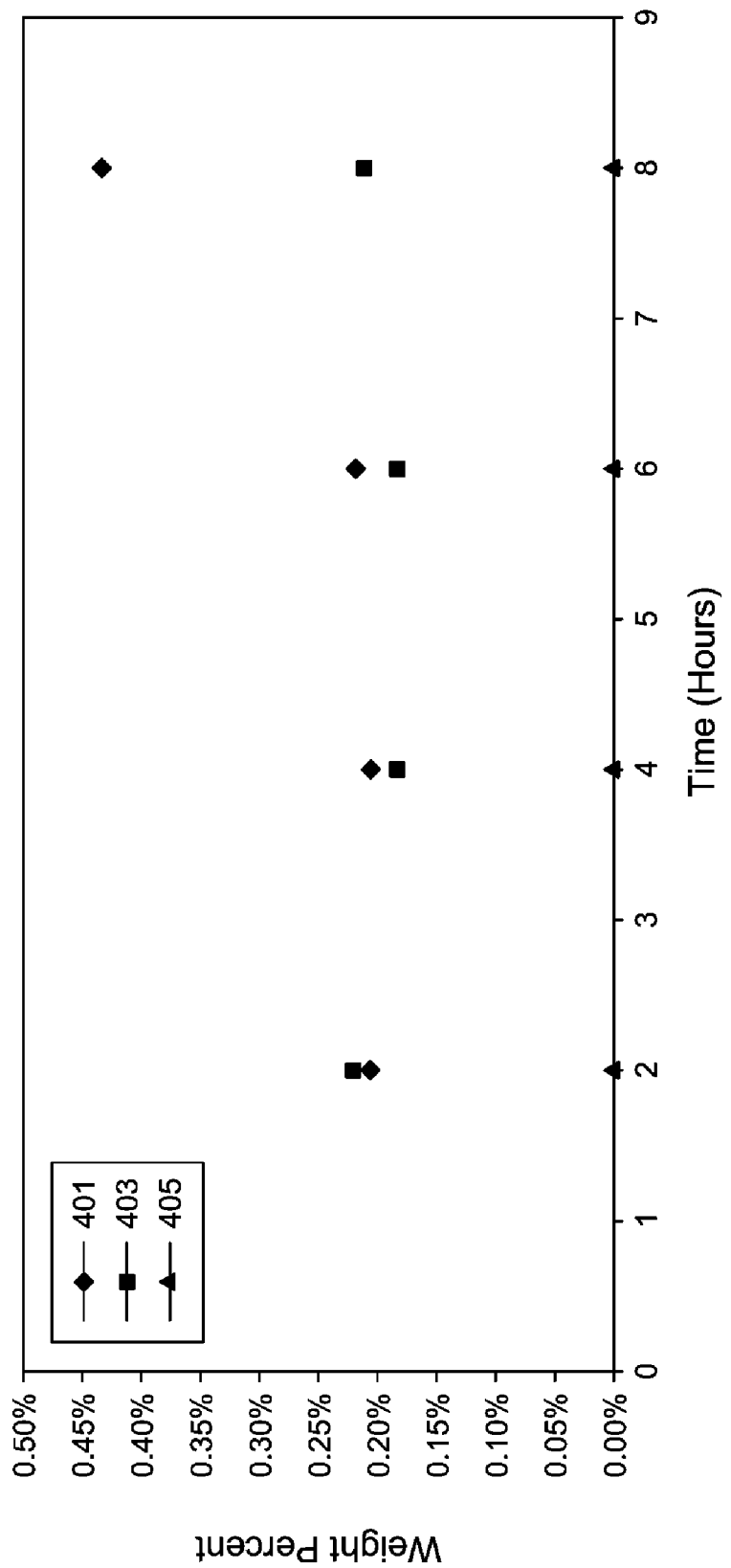
FIG. 4 is a graph showing the impact of water on the formation of the enol-ether of formula (IV) from cyclohexanone and phenol in the process of Example 2.
Figure 5:
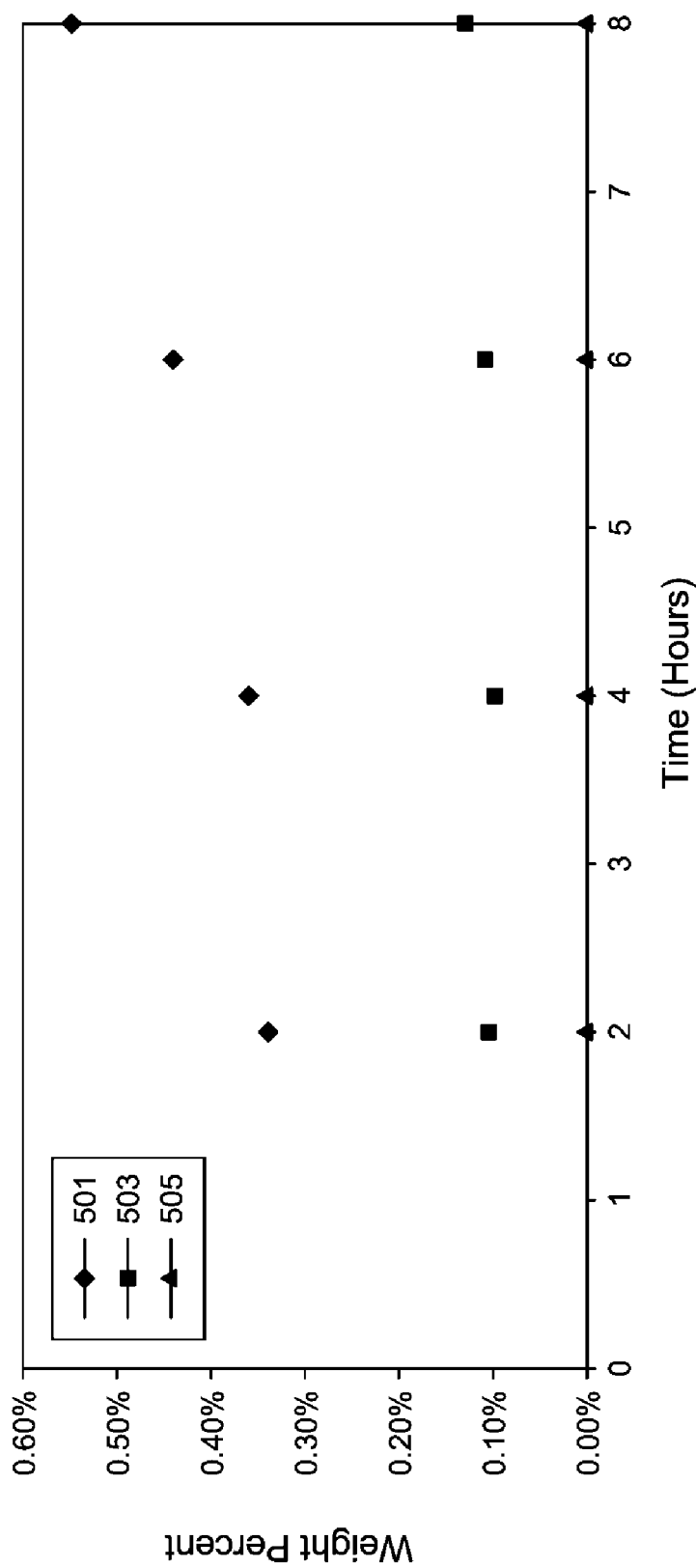
FIG. 5 is a graph showing the impact of water on the formation of the enol-ether of formula (VII) from cyclohexanone and phenol in the process of Example 2.

Another series of similar experiments to those of Example 1 were conducted on 100 gram mixtures of 15 wt % cyclohexanone, 15 wt % phenol, and 70 wt % DEG, in the absence of any catalyst, and refluxed for 8 hours. A part of this series of experiments included introducing water into the matrix, either before or after heating to about 133° C. or above (the presence of the water affects the boiling point of the mixture at atmospheric pressure and temperatures were adjusted accordingly for a given experiment). When nine grams of water were added to the 100 g mixture after heating to 133° C. for 8 hours, there was no sign that the reaction of cyclohexanone and DEG was reversed, i.e., the concentrations of the enol-ethers of Formulas (IV) and (VII) did not change. However, adding six grams of water to a 100 gram mixture before heating to the bubble temperature for eight hours suppressed the reaction of cyclohexanone and DEG completely, and no enol-ether products were seen. An addition of three grams of water to the 100 grams of mixture before heating to its bubble temperature inhibited the reaction by approximately 50% relative to the corresponding experiment where no water was introduced. The concentrations of the enol-ethers of Formulas (IV) and (VII) with time in these experiments, where no water was added and where water was added prior to heating, are shown in FIGS. 4 and 5, respectively. The weight percentages are with respect to the 100 gram starting mixture plus added water, if any. In FIG. 4, data points indicated by symbols 401, 403, and 405 are results of experiments run with no water, 3 grams of water, and 6 grams of added water, respectively. In FIG. 5, data points indicated by symbols 501, 503, and 505 are results of experiments run with no water, 3 grams of water, and 6 grams of added water, respectively.

Example 3

The experiments described in Example 3 monitor the formation of the enol-ethers of Formulas (IV) and (VII) from diethylene glycol and cyclohexanone in a large-scale extractive distillation process for the separation of a mixture of phenol and cyclohexanone. No added water was present in these extractive distillation experiments.

Figure 6:
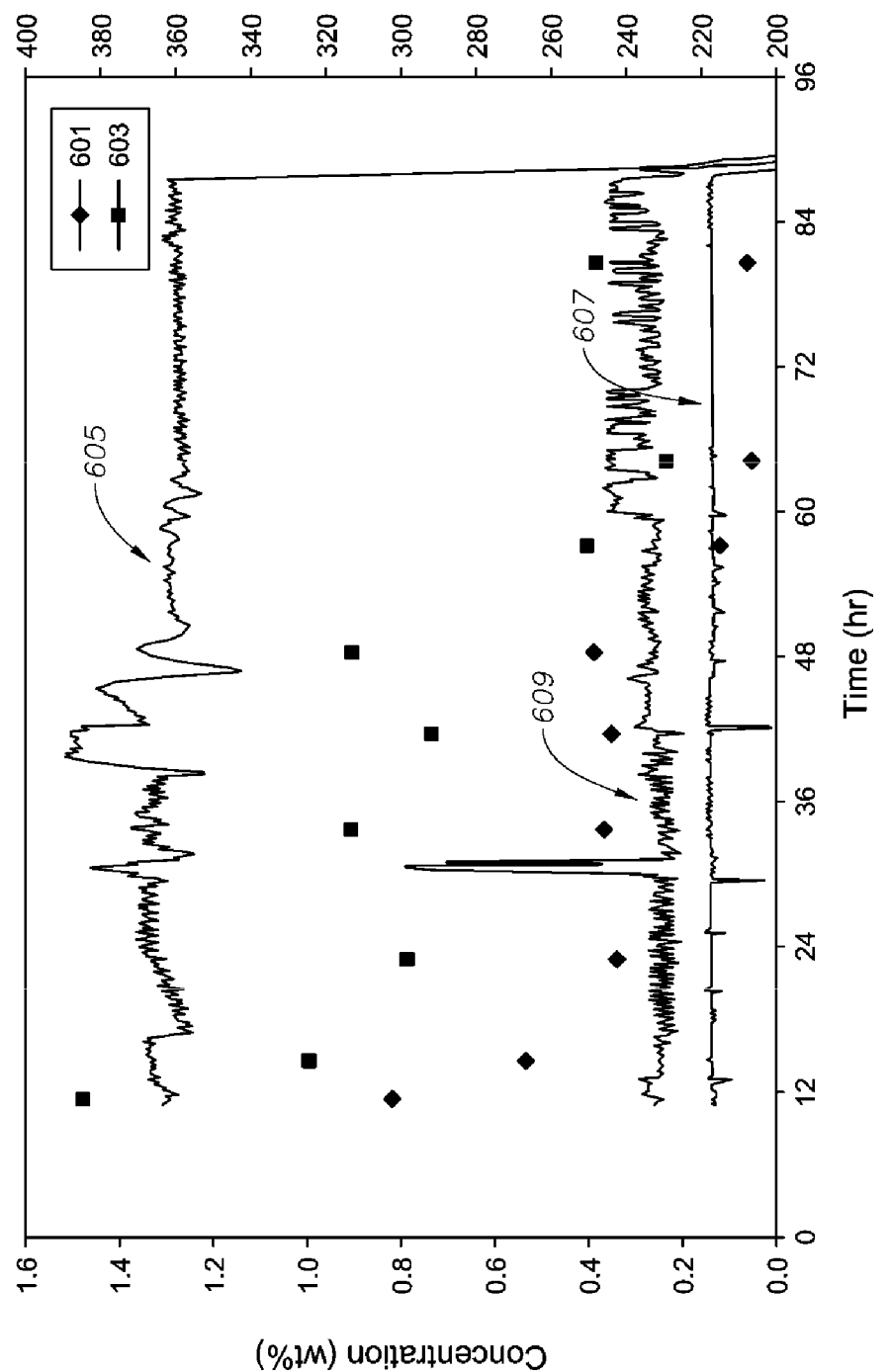
FIG. 6 is a graph showing the changes in concentration of the enol-ethers of formulas (IV) and (VII) with time in the extractive distillation process of Example 3.

The following description refers to FIG. 6, providing information on some pertinent temperatures within the extractive distillation column and concentration of the enol-ethers of Formulas (IV) and (VII) in the bottoms product. In FIG. 6, the symbol designated 601 is the concentration of the enol-ether of Formula (IV) (on the GC apparatus having a retention time of 38.7 minutes), the symbol designated 603 is the concentration of the enol-ether of Formula (VII) (on the GC apparatus having a retention time of 58 minutes), and both correspond to the left hand scale. The curved line designated 605 is the bottoms product temperature in the reboiler, the curved line designated 607 is temperature taken at a point in the column about 4 feet from the top of packing, and the curved line 609 is temperature taken at a point in the column about 1 foot below the feed point (about 9 feet from the top of packing), and all correspond to the right hand scale in degrees Fahrenheit (° F.).

The extractive distillation column was 2 inches in diameter, outfitted with a reboiler and full condensor, and included 16 feet of Pro-Pak® 0.24 inch protruded packing within the column along with periodic liquid distributers within the length of the packing, estimated to provide from about 50 to about 80 actual separation plates. The column also had means to continuously introduce a fresh feed into the center of the packing (about 8 feet below the top of the packing), and continuously provide reflux and remove an overhead product from the condensor and remove a bottoms product from the reboiler. Further, the column configuration was such that any water produced within the column, and present as free water after condensing material in the condensor, was isolated and not returned to the column with the reflux or present in the overhead product. Finally, the column also had means to recycle the overhead and bottoms products fully (with the exception of any free water just noted) as the feed to the column, replacing completely the fresh feed, so as to operate the continuous column in a batch type fashion and demonstrate the effect of introducing enol-ethers into the feed of the column. The condenser was fitted with a vacuum pump to allow the column to operate at subatmospheric pressure.

A mixture of phenol and cyclohexanone, 50 wt % of each, was prepared in one feed tank, and fresh diethylene glycol as a solvent was loaded into another feed tank. The column was charged with 100 grams of the mixture and 300 grams of the solvent from the tanks, and flow from the tanks was stopped. The whole process started at 12:00 AM on Day 1. At about 9:00 AM on Day 1, heat was applied to the reboiler and cooling to the condenser, and conditions were adjusted until the column was operating at a condenser pressure of about 1.5 psia and an overhead and bottoms product were available, which were both recycled in their entirety to the feed point (both the overhead and bottoms were mixed in a tube that entered the column at the feed location). It will be noted on FIG. 6 that the enol-ethers of Formulas (IV) and (VII) were formed in the column once heat was applied.

Conditions of the column continued to be adjusted until a reflux to overhead product ratio of 1.0 was obtained, with the result being that the overhead product was almost pure cyclohexanone, containing less than 1200 wppm of phenol and no detectable solvent, hemi-ketal and enol-ethers, and that the bottoms product was substantially only phenol, solvent, and enol-ethers, containing less than 250 wppm of cyclohexanone. The column reached a stable operating condition at about 8:00 PM on Day 1 with the column on total recycle as described. Note that the enol-ethers found in the bottoms product were being recycled to the feed of the column, and remarkably, the concentration of both in the bottoms product did not change (within the normal level of analytical error and operating condition deviations), demonstrating that no additional enol-ether was formed. Thus, the use of recovered solvent containing enol-ethers in the extraction eliminates the additional formation of enol-ethers in the extraction, preventing additional loss of valuable cyclohexanone and solvent.

Operations in this stable, total recycle mode continued until about 6:00 AM on Day 3, at which point the total recycle operation was ceased and transitioned to continuous feed operations, wherein 100 grams per hour of mixture and 300 grams per hour of fresh solvent were continuously fed to the column, again combined and provided to the feed point in the column. The overhead and bottoms products were continuously removed from the column and provided to other product tanks. Conditions in the column were adjusted to maintain similar compositions of phenol overhead and cyclohexanone in the bottoms products as established during the total recycle operation, and a stable, continuous feed operation was reached at about 9:00 AM that same day at a reflux to overhead product ratio of 1.0. Note that the concentration of the enol-ethers drop, attributable to the continuous withdrawal of the bottoms product from the column, but maintained a relatively constant level, indicating that they are continuously being formed in the column from the substantially pure cyclohexanone and diethylene glycol fed to the column when enol-ethers are not present in the feed to the column (and thus, cyclohexanone and solvent are being continuously lost to new enol-ethers). Also, note the response of the reboiler temperature (605) to the changes in concentration of enol-ether, with higher temperatures at higher concentrations.

The experiment was ended about noon on Day 4, when feed and product flows were stopped and heat ceased to the reboiler.

The invention claimed is:

1. A process for separating cyclohexanone and phenol, the process comprising:
  (a) feeding to a distillation column a mixture comprising (i) cyclohexanone, (ii) phenol, (iii) a solvent including at least two alcoholic hydroxyl groups attached to non-adjacent saturated carbon atoms, and (iv) at least one hemiketal defined by the formula (I) or the formula (II), and/or at least one enol-ether derived from the hemiketal defined by the formula (I) or the formula (II):

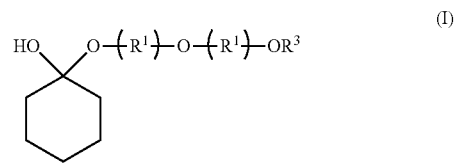

-continued

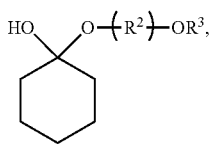 (II)

wherein $R^1$, the same or different at each occurrence, is independently an alkylene group having from 2 to 10 carbon atoms, $R^2$ is an alkylene group having from 4 to 10 carbon atoms, and $R^3$ is hydrogen or the following group:

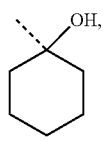

wherein the total concentration of the hemiketal and enol-ether in the mixture, expressed in terms of weight percentage on the basis of the total weight of the mixture, is at least 0.01%; and (b) distilling at least a portion of the mixture in the distillation column.

2. The process of claim 1, wherein the total concentration of the hemiketal and the enol-ether in the mixture is at least 0.10%.

3. The process of claim 1, wherein said solvent is diethylene glycol and $R^1$ is an ethylene group.

4. The process of claim 3, wherein said hemiketal is defined by the formula:

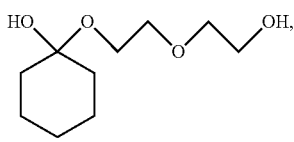

and said enol-ether thereof is defined by the formula:

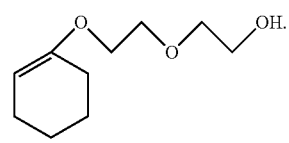 [SMILES: OCCOCCOC1=CCCCC1]

5. The process of claim 3, wherein said hemiketal is defined by the formula:

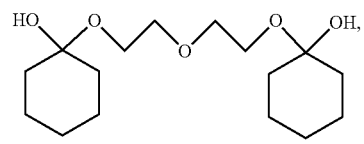 [SMILES: OC1(OCCOCCOC2(O)CCCCC2)CCCCC1]

and said enol-ether thereof is defined by the formula:

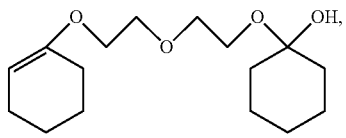 [SMILES: OC1(OCCOCCOC2=CCCCC2)CCCCC1]

and/or by the formula:

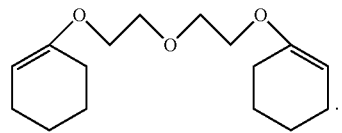 [SMILES: C1=C(OCCOCCOC2=CCCCC2)CCCC1]

6. The process of claim 1, wherein said solvent is 1,4-butanediol and $R^2$ is 1,4-butylene.

7. The process of claim 6, wherein said hemiketal is defined by the formula:

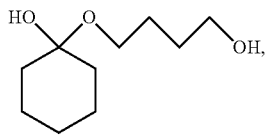

and said enol-ether thereof is defined by the formula:

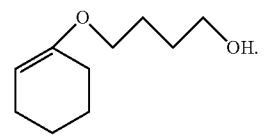 [SMILES: OCCCCOC1=CCCCC1]

8. The process of claim 6, wherein said hemiketal is defined by the formula

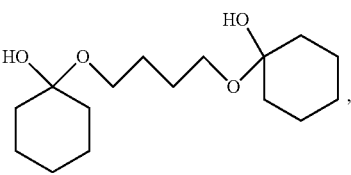

and said enol-ether thereof is defined by the formula:

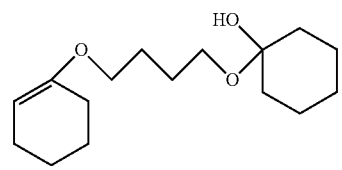 [SMILES: OC1(OCCCCOC2=CCCCC2)CCCCC1]

and/or by the formula:

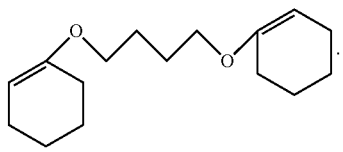 [SMILES: C1=C(OCCCCOC2=CCCCC2)CCCC1]

9. The process of claim 1, wherein said distilling (b) step (a) is conducted in the presence of water.

10. The process of claim 9, wherein water is present in an amount in the range from 0.1 wt % to 20 wt %, based on the total weight of the mixture fed to the distilling (b).

11. The process of claim 1, wherein said distilling (b) separates the mixture into a first stream rich in cyclohexanone and a second stream rich in phenol, the solvent, and said hemiketal and/or enol-ether.

12. The process of claim 11, further comprising (c) distilling said second stream to separate at least part of the phenol therefrom and produce a recovered solvent.

13. The process of claim 12, wherein the recovered solvent further comprises said hemiketal and/or enol-ether and provides at least a portion of said hemiketal and/or enol-ether present in the mixture.

14. A process for making phenol and cyclohexanone, the process comprising:
(A) contacting benzene and hydrogen with a catalyst under hydroalkylation conditions to produce a first effluent comprising cyclohexylbenzene;
(B) oxidizing at least part of the cyclohexylbenzene in the first effluent to produce a second effluent comprising cyclohexylbenzene hydroperoxide;
(C) cleaving at least part of the cyclohexylbenzene hydroperoxide in the second effluent stream to obtain a product mixture comprising phenol and cyclohexanone; and
(D) separating the product mixture by
(a) feeding to a distillation column a charge comprising (i) at least a portion of the mixture, (ii) a solvent including at least two alcoholic hydroxyl groups attached to non-adjacent saturated carbon atoms, and (iii) at least one hemiketal defined by one the formulae (I), (II), and/or at least one enol-ether derived from the hemiketal defined by the formula (I) or the formula (II):

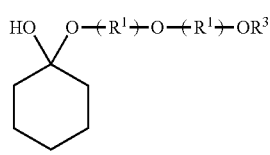 (I)

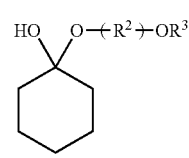 (II)

wherein $R^1$, the same or different at each occurrence, is independently a branched or straight-chain alkylene group having from 2 to 10 carbon atoms, $R^2$ is a branched or straight-chain alkylene group having from 4 to 10 carbon atoms, and $R^3$ is hydrogen or the following group:

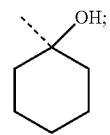

and
(b) distilling at least a portion of the charge in the distillation column.

15. The process of claim 14, wherein $R^1$ is ethylene and $R^2$ is 1,4-butylene.

16. A composition of matter comprising: (i) phenol, (ii) cyclohexanone, (iii) a solvent including at least two alcoholic hydroxyl groups attached to non-adjacent saturated carbon atoms, and (iv) 0.01 wt % to 10 wt %, based on the total weight of the composition, of a hemiketal defined by the formula (I) and/or an enol-ether derived from the hemiketal defined by the formula (I):

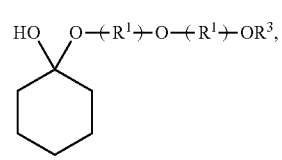 (I)

wherein $R^1$, the same or different at each occurrence, is independently an alkylene group having from 2 to 10 carbon atoms, $R^2$ is an alkylene group having from 4 to 10 carbon atoms, and $R^3$ is hydrogen or the following group:

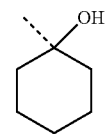

17. The composition of claim 16, wherein $R^1$ is an ethylene group.

18. The composition of claim 16, wherein $R^2$ is an alkylene group having 4 carbon atoms.

19. A composition of matter according to claim 16, the composition comprising a hemiketal defined by the formula (III):

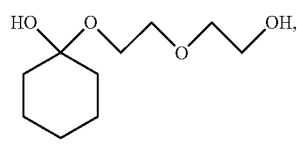 (III)

and/or an enol-ether thereof defined by the formula (IV):
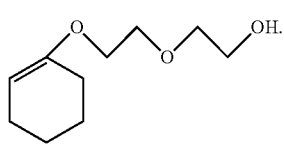
(IV)
20. A composition of matter according to claim 16, the composition comprising a hemiketal defined by the formula (V):
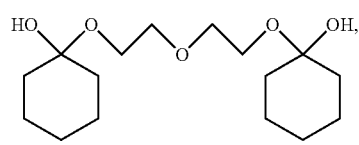
(V)
and/or an enol-ether thereof defined by the formula (VI):
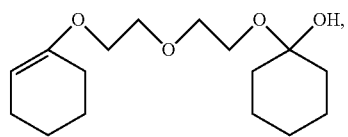
(VI)
and/or an enol-ether thereof defined by the formula (VII):
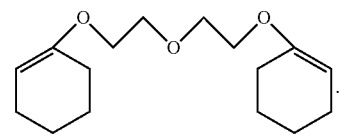
(VII)
* * * * *

UNITED STATES PATENT AND TRADEMARK OFFICE
CERTIFICATE OF CORRECTION

PATENT NO. : 9,464,020 B2  
APPLICATION NO. : 14/394208  
DATED : October 11, 2016  
INVENTOR(S) : Keith H. Kuechler et al.

Page 1 of 1

It is certified that error appears in the above-identified patent and that said Letters Patent is hereby corrected as shown below:

In the Claims

In Claim 9, Column 1, Line 11, please delete the phrase "step (a)".

Signed and Sealed this
Seventh Day of March, 2017

Michelle K. Lee
*Director of the United States Patent and Trademark Office*